United States Patent
Schwarz et al.

(10) Patent No.: US 7,524,327 B2
(45) Date of Patent: *Apr. 28, 2009

(54) LIGHT ACTIVATED GENE TRANSDUCTION USING LONG WAVELENGTH ULTRAVIOLET LIGHT FOR CELL TARGETED GENE DELIVERY

(75) Inventors: Edward M. Schwarz, Rochester, NY (US); Regis J. O'Keefe, Pittsford, NY (US); Thomas Foster, Rochester, NY (US); Jarod C. Finlay, Philadelphia, PA (US)

(73) Assignee: University of Rochester, Rochester, NY (US)

( * ) Notice: Subject to any disclaimer, the term of this patent is extended or adjusted under 35 U.S.C. 154(b) by 222 days.

This patent is subject to a terminal disclaimer.

(21) Appl. No.: 10/357,271

(22) Filed: Jan. 31, 2003

(65) Prior Publication Data

US 2003/0236394 A1 Dec. 25, 2003

Related U.S. Application Data

(60) Provisional application No. 60/353,842, filed on Jan. 31, 2002.

(51) Int. Cl.
*A61B 18/18* (2006.01)
(52) U.S. Cl. ............... 607/88; 607/89; 604/20; 435/448; 435/457; 435/460
(58) Field of Classification Search ............ 606/2, 606/3, 10–19; 607/88–94; 435/448, 456–460; 436/501

See application file for complete search history.

(56) References Cited

U.S. PATENT DOCUMENTS

| 4,671,273 A | 6/1987 | Lindsey |
|---|---|---|
| 4,846,172 A | 7/1989 | Berlin |
| 5,084,043 A | 1/1992 | Hertzmann et al. |
| 5,188,632 A | 2/1993 | Goldenberg |
| 5,201,729 A | 4/1993 | Hertzmann et al. |
| 5,242,439 A | 9/1993 | Larsen et al. |
| 5,340,734 A | 8/1994 | Della-Cioppa et al. |
| 5,604,090 A | 2/1997 | Alexander et al. |
| 5,834,182 A | 11/1998 | Alexander et al. |

(Continued)

FOREIGN PATENT DOCUMENTS

DE 34 15 293 A1 11/1985

(Continued)

OTHER PUBLICATIONS

Kulms et al; "Molecular mechanisms of UV-induced apoptosis"; Photodermatol Photomed; vol. 16; 2000; pp. 195-201.*

(Continued)

*Primary Examiner*—David Shay
(74) *Attorney, Agent, or Firm*—Knobbe Martens Olson & Bear LLP

(57) ABSTRACT

In accordance with the present invention, methods are provided for treating a patient through the use of ultraviolet light activated gene therapy. Embodiments of the present invention include methods for the utilization of light activated gene therapy to repair and/or rebuild damaged cartilage by introducing a desired gene into a patient's tissue.

24 Claims, 9 Drawing Sheets

U.S. PATENT DOCUMENTS

| | | | |
|---|---|---|---|
| 5,843,459 | A | 12/1998 | Link et al. |
| 6,149,896 | A | 11/2000 | Riklis et al. |
| 6,254,547 | B1 | 7/2001 | Phillips |
| 6,521,750 | B2 | 2/2003 | Hair et al. |
| 6,593,084 | B2 * | 7/2003 | Bird et al. ................ 436/501 |
| 6,632,002 | B1 * | 10/2003 | Chubb et al. ............... 607/88 |
| 6,900,197 | B2 | 5/2005 | Szabo |
| 2002/0168388 | A1 * | 11/2002 | Borchert et al. ........... 424/401 |
| 2003/0175959 | A1 * | 9/2003 | Fusenig et al. ............ 435/371 |
| 2005/0055072 | A1 | 3/2005 | Rubery et al. |

FOREIGN PATENT DOCUMENTS

| | | |
|---|---|---|
| DE | 4219626 | 12/1993 |
| DE | 43 36 989 A1 | 5/1995 |
| DE | 29716011 U | 10/1997 |
| EP | 0 152 686 A1 | 8/1985 |
| EP | 0680517 B2 | 1/2005 |
| WO | WO 89/03202 A2 | 4/1989 |
| WO | WO 99/47177 | 9/1999 |
| WO | WO 2004/069326 A | 8/2004 |

OTHER PUBLICATIONS

Pandori M.W. et al. Photoactivatable retroviral vectors: A strategy for targeted gene delivery. *Gene Therapy* Dec. 2000, vol. 7 No. 23 p. 1999-2006.

Koeberl, et al., "Persistent expression of human clotting factor IX from mouse liver after intravenous injection of adeno-associated virus vectors," *Proc. Natl. Acad. Sci. USA*, vol. 94, pp. 1426-1431 (1997).

Yang, et al., "Adeno-associated virus vector mediated transduction of primary normal human breast epithelial cells," *Oncology Reports*; 5:793-797 (1998).

Edward M. Schwarz, Ph.D., *The Adeno-Associated Virus Vector for Orthopaedic Gene Therapy*, Clinical Orthopaedics and Related Research, No. 379S, pp. S31-S39.

Goater et al., *Empirical Advantages of Adeno Associated Viral Vectors for in Vivo Gene Therapy for Arthritis*, J Rheumatol, 2000; vol. 27: pp. 983-989.

Alexander et al., *Effects of Gamma Irradiation on the Transduction of Dividing and Nondividing Cells in Brain and Muscle of Rats by Adeno-Associated Virus Vectors*, Human Gene Therapy, vol. 7; May 1, 1996: pp. 841-850.

Russell et al., *DNA synthesis and topoisomerase inhibitors increase transduction by adeno-associated virus vectors*, Proc. Natl. Acad. Scil USA; vol. 92, Jun. 1995: pp. 5719-5723.

Russell et al., *Adeno-associated virus vectors preferentially transduce cells in S phase*, Proc. Natl. Acad. Sci. USA; vol. 91, Sep. 1994: pp. 8915-8919.

Alexander et al., *DNA-Damaging Agents Greatly Increase the Transduction of Nondividing Cells by Adeno-Associated Virus Vectors*, Journal of Virology, Dec. 1994: pp. 8282-8287.

Alford et al. "Cartilage Restoration, Part 1" American Journal of Sports Medicine (2005), 33(2):295-306.

Evans et al. "Osteoarthritis gene therapy" Gene Therapy (2004) 11:379-389.

Ito et al. "Light-activated gene transduction of recombinant adeno-associated virus in human mesenchymal stem cells" Gene Therapy (2004) 11:34-41.

Madry et al. "Recombinant Adeno-Associated Virus Vectors Efficiently and Persistently Transduce Chondrocytes in Normal and Osteoarthritic Human Articular Cartilage." Human Gene Therapy (2003) 14:393-402.

Pan et al. "Disease-Inducible Transgene Expression from a Recombinant Adeno-Associated Virus Vector in a Rat Arthritis Model." Journal of Virology (1999) pp. 3410-3417.

Trippel et al. "Gene-based approaches for the repair of articular cartilage." Gene Therapy (2004) 11:251-359.

Ulrich-Vinther et al. "Light-Activated Gene Transduction Enhances Adeno-Associated Virus Vector-Mediated Gene Expression in Human Articular Chondrocytes." Arthritis & Rheumatism (2002) 46(8): 2095-2104.

Yang et al. "ATM, ATR and DNA-PK: initiators of the cellular genotoxic stress responses." Carcinogenis (2003) 24(10):1571-1580.

Zhang et al. "Requirement of ATM in UVA-induced Signaling and Apoptosis." J Biological Chem (2002) 277(5): 3124-3131.

Ito et al., Light activated gene transduction of recombinant adeno-associated virus in human mesenchymal stem cells Gene Therapy 11:34-41 (2004).

Office Action received in U.S. Appl. No. 10/769,392, dated Aug. 29, 2007, in 15 pages.

Ariizuma et al. Wavelength-specific induction of immediate early genes by ultraviolet radiation, Journal of Dermatological Science, 12(1996): 147-155.

Communication Pursuant to Article 96(2) EPC; received in European Appl. No. 04707090.9; dated Mar. 15, 2007, 7 pages.

Miyamoto et al. "Ultraviolet Cross-Linking of DNA Binding Proteins", Methods in Enzymology, 1995, vol. 254, p. 632-641.

Office Action dated Feb. 14, 2008, received in U.S. Appl. No. 10/769,392, 9 pages.

Peak et al. "DNA-to-Protein Crosslinks and Backbone Breaks Caused by Far- and Near-Ultraviolet, and Visible Light Radiations in Mammalian Cells", Basic Life Sciences, 1986. vol. 38, p. 193-202.

Han et al. "Induction of DNA-protein cross-linking in Chinese hamster cells by monochromatic 365 and 405 nm ultraviolet light" Photochemistry and Photobiology 1984, 39(3) 343-348.

Peak et al. "Induction of DNA-protein crosslinks in human cells by ultraviolet and visible radiations: action spectrum" Photochemistry and Photobiology, 1985, 41(3) 295-302.

File History of U.S. Appl. No. 10/357,273, filed Jan. 31, 2003.

File History of U.S. Appl. No. 10/942,353, filed Sep. 15, 2004.

File History of U.S. Appl. No. 10/769,392, filed Jan. 30, 2004.

Extended European Search Report, European Appl. No. 08101769.1, dated May 28, 2008, 6 pages.

Office Action dated Jul. 9, 2008, received in U.S. Appl. No. 10/942,353.

Summary Statement, 9 pages.

Nakai et al. "Extrachromosomal Rembinant Adeno-Associated Virus Vector Genomes Are Primarily Responsible for Stable Liver Transduction In Vivo," Journal of Virology, Aug. 2001, p. 6969-6976.

Nakai et al. "Unrestricted Hepatocyte Transduction with Adeno-Associated Virus Cerotype 8 Vectors in Mice." Journal of Virology, Jan. 2005, p. 214-224.

Jiang et al. "Effects of transient immunosuppression on adenoassociated, virus-mediated, liver-directed gene transfer in rhesus macacques and implications for human gene therapy." Blood (2006), 108:3321-3328.

Manno et al. "Successful transduction of liver in hemophilia by AAV-Factor IX and limitations imposed by the host immune response." Nature Medicine, Mar. 2006, 12(3): 342-347, 592.

Supplementary European Search Report, European Appl. No. 06 124 972.8—1223, dated Nov. 14, 2007, 8 pages.

Office Action dated Sep. 7, 2007, received in U.S. Appl. No. 10/357,273, in 5 pages.

Alberts et al, *Molecular Biology of the Cell*, 4th Ed, 2002, pp. 267-269.

Glen Research Glen Report, "Thymine Dimers—DNA Lesions Induced by Sunlight CIS-SYN Thymine Dimer Phosphoramidite Now Available" Dec. 17, 2003; accessed Oct. 27, 2005 from http://glenres.com/GlenReports/GR16-21.html, 2 pages.

Kornberg et al, DNA Replication, 2nd Ed, 1992, p. 772.

Stryer, *Biochemistry*, 2nd ed., 1981, pp. 587-588.

Vink et al. Biological consequences of cyclobutane pyrimidine dimmers. J Photochem & Photobiol B Biol, 2001, 65:101-104.

Zubay, *Biochemistry*, 1983, pp. 768-771.

Office Action dated Apr. 19, 2007, in U.S. Appl. No. 10/357,273.

* cited by examiner

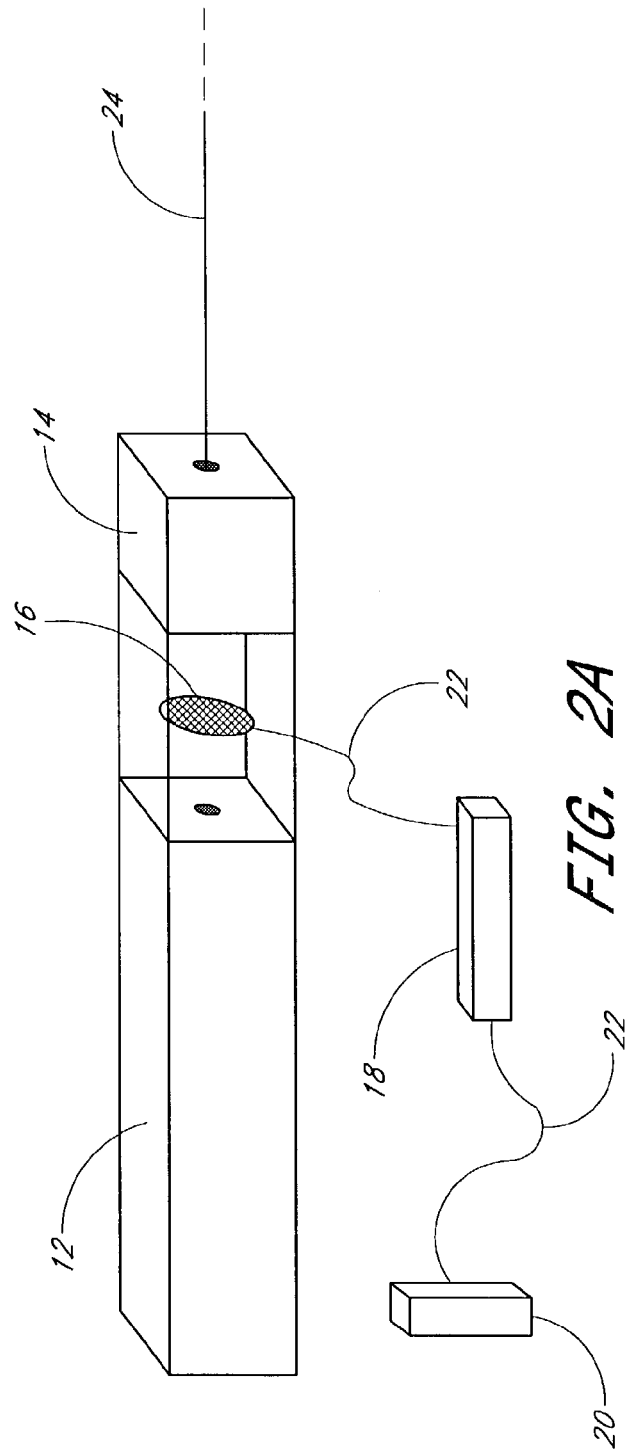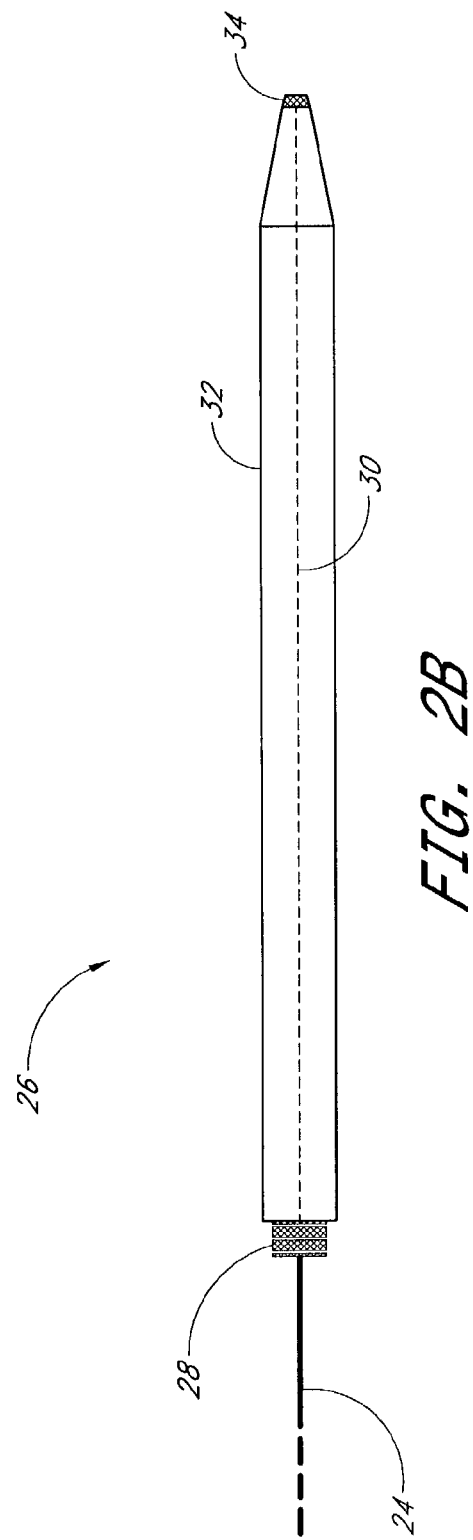

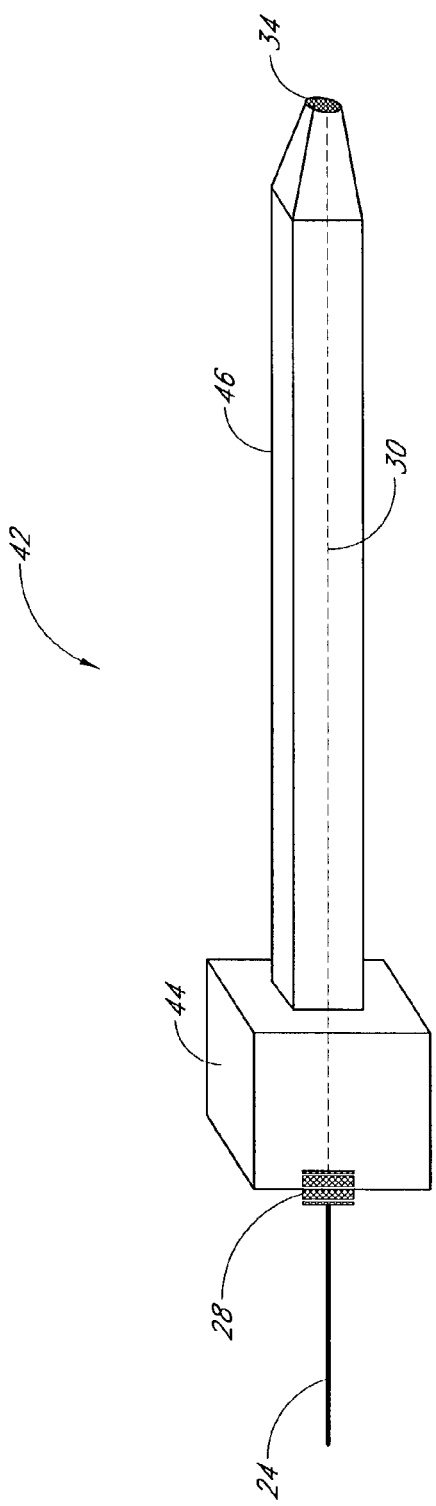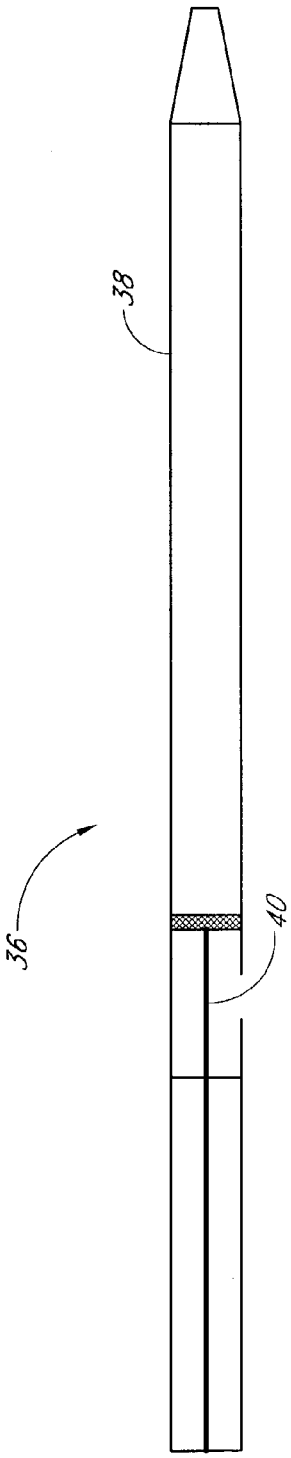
FIG. 2C
FIG. 3

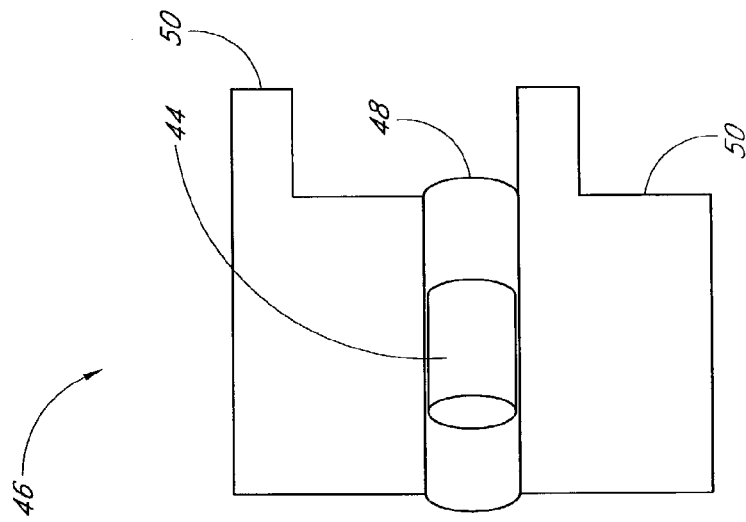
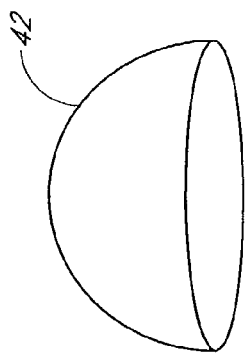
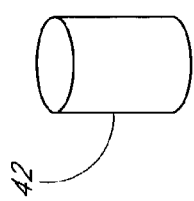

LIGHT ACTIVATED GENE TRANSDUCTION USING LONG WAVELENGTH ULTRAVIOLET LIGHT FOR CELL TARGETED GENE DELIVERY

REFERENCE TO RELATED APPLICATIONS

The present application claims the priority benefit under 35 U.S.C. §119(e) of Provisional Application No. 60/353,842, filed on Jan. 31, 2002. The present application is also related to Provisional Application No. 60/353,907, filed on Jan. 31, 2002, and U.S. application Ser. No. 10/357,273, filed on Jan. 31, 2003.

GOVERNMENT INTEREST

This invention was made with Government support under NIH Contract #AR45971, an ROI grant awarded by NIAMS. The Government has certain rights in the invention.

BACKGROUND OF THE INVENTION

1. Field of the Invention

The invention relates generally to the field of gene therapy. According to the present invention, devices and methods are provided for the combined use of light activated gene transduction (LAGT) employing ultraviolet light and recombinant adeno-associated virus (r-AAV) for the purpose of introducing a desired gene into a patient's tissue.

2. Description of the Related Art

Somatic cell gene therapy is a form of treatment in which the genetic material of a target cell is altered through the administration of nucleic acid, typically in the form of DNA. In pursuit of effective in vivo administration routes, scientists have harnessed the otherwise potentially deleterious ability of viruses to invade a target cell and "reprogram" the cell through the insertion of viral DNA. By encapsulating desirable genetic material in a viral particle, or "vector," minus some of the viral DNA, the effective and targeted delivery of genetic material in vivo is possible. As applied to specific treatments, gene therapy offers the ability to adjust the expression of desirable molecules, including both intracellular and extracellular proteins, to bring about a desired biological result.

In particular, the desirable qualities of adeno-associated viruses (AAV) have led to further study of potential gene therapy uses. As a vehicle for gene therapy recombinant forms of AAV, or r-AAV, offer many advantages including the vector's ability to infect non-dividing cells (e.g., chondrocytes, cells within cartilage), the sustained target gene expression, the low immune response to the vector, and the ability to transduce a large variety of tissues. The AAV contains a single strand DNA (ssDNA) genome. Under normal conditions AAV is present in humans in a replication incompetent form, due to the fact the AAV alone does not encode the enzyme required for replication of the second DNA strand. Successful r-AAV transduction often requires the presence of a co-infection with an adenovirus or the exposure of the host cell to DNA damaging agents, such as γ-irradiation. The introduction of either the co-infection or the DNA damaging agents dramatically induces the rate limiting step of second strand synthesis, i.e. the second strand of DNA which is synthesized based on the vector inserted first strand. However, making use of these DNA damaging agents is impractical because the administration of an adenovirus co-infection to a patient is not practical or desirable and the site specific and safety issues involved with using γ-irradiation undesirable as well.

In the past, attempts have been made to induce r-AAV transduction in vitro using UV radiation having a wavelength of 254 nm. Unfortunately, no effective therapeutic method or apparatus was developed based on these experiments due to the long exposure times involved with using 254 nm UV radiation, the difficulties of delivering 254 nm UV radiation to a surgical target site, and the inability to position the 254 nm UV light source so as to allow effective penetration of a target cell.

SUMMARY OF THE INVENTION

Preferred embodiments of the present invention provide structures and methods for treating a patient using light activated gene therapy.

In accordance with an embodiment of the present invention, a method of introducing a desired gene into a patient's tissue is provided. The method includes locating a light probe proximate to the target cells. A long wavelength ultraviolet light is then transmitted through a light delivery cable to the light probe. Transduction of the ultraviolet light activated viral vector in target cells is activated using the light probe. An ultraviolet light activated viral vector is delivered proximate to target cells.

In accordance with another embodiment of the present invention, a gene therapy system for increasing the transduction of an ultraviolet activated viral vector is provided. The system includes a light source capable of long wavelength ultraviolet light output and a light probe configured to access an appropriate treatment site. An optical delivery cable is also provide to transmit the ultraviolet light from the light source to the light probe. In addition, light channeling optics are included to channel the light output into the light delivery cable.

In accordance with yet another embodiment of the present invention, a long wavelength ultraviolet radiation treatment system for increasing the transduction of an ultraviolet light activated viral vector in a patient's target cells is provided. The system includes a power source which powers a light source producing a long wavelength ultraviolet light beam. A timed shutter with a shutter control interface is included to selectively block the light beam. In addition, an optical coupler for channeling the light beam into a light delivery cable. A light probe, which is operatively connected to the light delivery cable, is configured to selectively output the light beam. Furthermore, the light probe is also configured to access the target cells.

In accordance with still another embodiment of the present invention, an implant system for introducing a desired gene into a patient's tissue is provided. The system includes an implant configured to be inserted into a patient's tissue in a minimally intrusive surgical procedure and an ultraviolet activated viral vector which is integrated with the implant.

A feature of certain preferred embodiments of this invention is the avoidance of the problems involved with using UV and γ-irradiation through the use of locally administered, long wavelength UV (i.e., greater than or equal to 255 nm) radiation in order to induce the target cell to more effectively stimulate the transduction of a UV activated viral vector, such as recombinant adeno-associated virus (r-AAV).

BRIEF DESCRIPTION OF THE DRAWINGS

FIG. 2A is a side view schematic of a component of a long wavelength UV radiation system, including a light source and user interface.

FIG. 2B is a schematic of another component of the long wavelength UV radiation system, including a light probe, which in conjunction with the light source and user interface shown in FIG. 2A, forms the in vivo long wavelength UV radiation system, in accordance with another embodiment of the present invention.

FIG. 2C is perspective schematic of an external light probe which, in conjunction with the component having the light source and user interface shown in FIG. 2A, forms the ex vivo long wavelength UV radiation system configured for external applications, in accordance with an alternate embodiment of the present invention.

FIG. 3 is a schematic of an injecting device for introducing a UV activated vector into a patient's tissue, in conjunction with the long wavelength UV radiation system, shown in FIGS. 2A and 2B.

FIGS. 5A-5D are perspective schematics of implants for use in conjunction with the long wavelength UV radiation systems and method provided herein, in accordance with another embodiment of the present invention.

FIG. 5E is a cross-section schematic of the expanded implant of FIG. 6D, the expanded implant shown located between two vertebra.

DETAILED DESCRIPTION OF THE PREFERRED EMBODIMENT

The term "AAV" refers to adeno-associated virus, while "r-AAV" refers to recombinant adeno-associated virus. Preferably, r-AAV includes only the desired gene to be introduced into the patient's tissue and the flanking AAV inverted terminal repeats (ITRs) that serve as the packaging signals.

"Ultraviolet radiation" and "ultraviolet light," also known as "UV", refer to the portions of the electromagnetic spectrum which have wavelengths shorter than visible light. The range of wavelengths considered to be ultraviolet radiation, from about 4 nanometers to about 400 nanometers, is further subdivided into three subgroups, UVA, UVB, and UVC. "UVA" is the portion of ultraviolet radiation which includes wavelengths from 320 nm up to and including 400 nm. "UVB" is the portion of ultraviolet radiation which includes wavelengths from 280 nm up to and including 320 nm. "UVC" is the portion of ultraviolet radiation having a wavelength less than 280 nm.

The term "long wavelength UV" refers to ultraviolet radiation or light having a wavelength equal to or greater than 255 nm, but not more than 400 nm.

A "viral vector" refers to a virus, or recombinant thereof, capable of encapsulating desirable genetic material and transferring and integrating the desirable genetic material into a target cell, thus enabling the effective and targeted delivery of genetic material both ex vivo and in vivo. A. "UV activated viral vector" "UV light activated viral vector" is any virus, or recombinant thereof, whose replication is regulated by ultraviolet light. Recombinant adeno-associated virus (r-AAV) is included in the group of viruses labeled UV activated viral vectors. A "solid platform" is any structure designed to be inserted into the body for the purpose of aiding the treatment of the target site proximate to where the solid platform is inserted.

The term "LAGT" refers to light activated gene transduction, while "LAGT probe" or "light probe" or "long UV wavelength light probe" refers to the medical device which delivers long wavelength ultraviolet light to the target site and effectuates the transduction of the desired gene carried by the vector.

Figure 1:
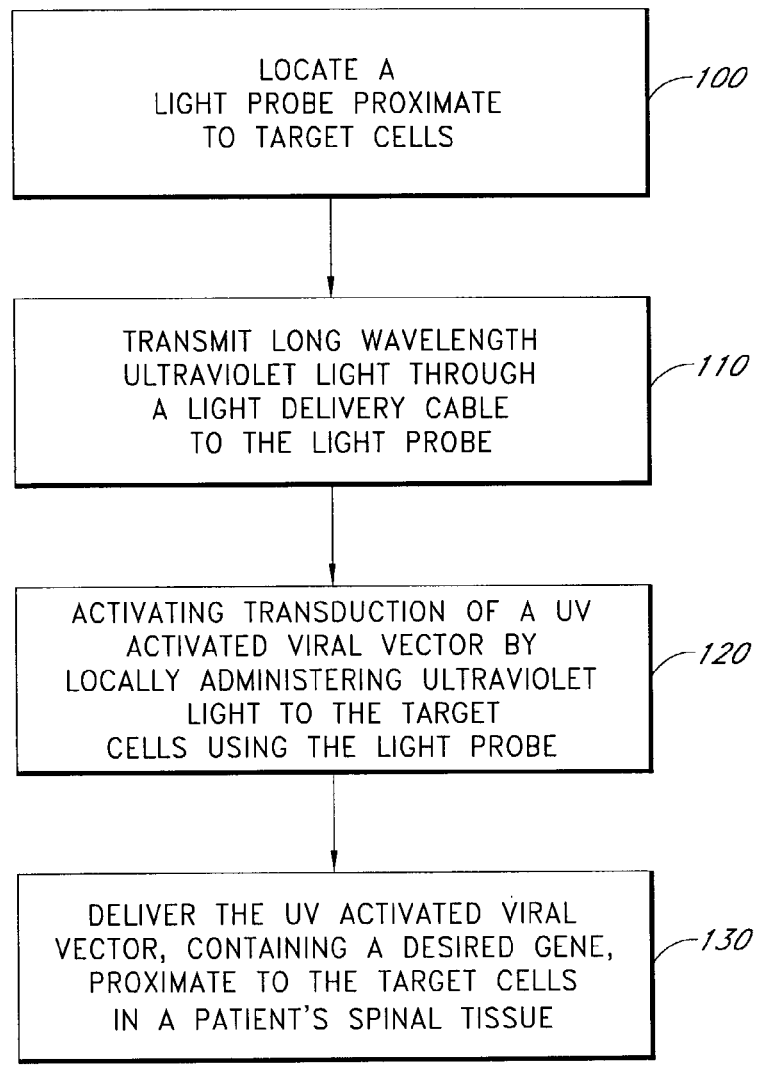
FIG. 1 is flowchart of a method of treating target cells in a patient's tissue by activating the transduction of a UV light activated viral vector using a light probe, in accordance with an embodiment of the present invention.

With reference to FIG. 1, a method of treating a patient's tissue is shown. A light probe is located 100 proximate to target cells. Long wavelength ultraviolet (UV) light is then transmitted 110 through a light delivery cable to the light probe. The transduction of the viral vector is activated 120 by locally administering ultraviolet light to the target cells using the light probe. Preferably, the wavelength of the UV light ranges from about 255 nm up to and including about 400 nm. A UV activated viral vector containing a desired gene is delivered 130 proximate to target cells in a patient's tissue. In other preferred embodiments, the wavelength of the UV light ranges from about 280 to about 330. More preferably, the locally administered UV radiation has a wavelength from about 315 nm to about 355 nm, most preferably about 325 nm. In an alternate embodiment the ultraviolet radiation has a wavelength of about 4 nm to about 400 nm, while in another alternate embodiment the ultraviolet radiation has a wavelength of 290 nm.

It should be noted that the method of FIG. 1 may be performed in other preferred embodiments in a different order than the textually outlined above. For example, in another preferred embodiment the vector is delivered prior to locally administering the ultraviolet light.

FIGS. 2A-2C illustrate separate components of a UV radiation delivery system, with FIG. 2A showing the UV light generator 10, user interface system, and FIG. 2B and FIG. 2C showing in vivo and ex vivo versions, respectively, of the light probe 26, 42. Note the light probe 26, 42 is operatively connected to the UV light generator 10 by the light delivery cable 24.

FIG. 2A shows a UV radiation delivery system including a light source 12 with sufficient long wavelength UV output. In addition, light channeling optics, such as an optical coupler 14, transmit the light from the light source 12 into a light delivery cable 24, such as an optical fiber cable or bundle that transmits the light to an target site, for in vivo purposes, via a light probe 26 (FIG. 2B). A timed shutter 16 is located in the path of the light beam between the light source 12 and the optical coupler 14 in order to control the length of time the patient is exposed to UV light via the light probe 26 (FIG. 2B). The timed shutter 16 is operatively connected via connectors 22 to a shutter controller 18 and a shutter control interface 20. Note that the in vivo light probe 26 disclosed in FIG. 2A can, in alternate embodiments in which ex vivo treatment is desirable, be interchanged with an ex vivo light probe shown in FIG. 2C.

FIG. 2B shows a light probe 26 as part of an in vivo UV radiation delivery system for use with the light source and user interface, such as those shown in FIG. 2. The light probe 26 is configured to locally irradiate target cells, infected by a UV activated viral vector, with long wavelength ultraviolet (UV) light. The light probe 26 is joined to the light delivery cable by an optical connector 28. The light probe 26 is configured to fiber-optically transmit an appropriate UV wavelength light, which originates from the light source 12, through a light guide 30 to a light guide terminator 34, such as a microlens tip or cylindrical diffusing lens tip, in order to "activate" r-AAV transduction in target cells. The light probe 26 is preferably both shaped in the form of an arthroscope and interchangeable with light probes having a differing configurations. For example, the light probe can be configured to have different forms in order to more effectively access different treatment sites. Preferably, the optical connector 28 allows the light probe 26 to be selectively detached from the light delivery cable 24 when desired. In certain alternate embodiments, the UV radiation delivery system also includes a targeting laser beam (not shown) to enable accurate delivery of the light. Standard surgery tools as recognized by those skilled in the art, for example cannulas and trochars, may also be incorporated into the disclosed method. Preferably, the light probe 26 is configured to be sterile and disposable.

In the embodiment shown in FIG. 2A, the light source 12 is contained within a housing, while in certain alternate embodiments the light source 12 is operatively joined to the housing. It should be understood that the exact shape and size of the light probe 26 shown in FIG. 2A, and especially the light probe tip, will vary depending on the particular application and target site as would be understood by one skilled in the art. For example, the light probe 26 can be configured to access an intervertebral disc in a patient's spine or the cartilage in a patient's joint. The preferred embodiments include a light source comprising a laser tuned to the appropriate long UV wavelength. In preferred embodiments, the UV radiation delivery system, whether it be a lamp or laser based system, will be optimized based on considerations such as cost and technical simplicity. In addition, the lamp delivery system can also include a targeting laser beam to enable accurate delivery of the light. Standard surgery tools, for example cannulas and trochars, may also be used.

As shown in FIG. 2C, in accordance with alternate preferred embodiments, an ex vivo light probe 42 for use with the light source and user interface component of FIG. 2A is provided to form an ex vivo UV radiation system. In this ex vivo embodiment, the light probe 42 is designed for non-surgical use, such as the irradiation of a patient's skin or irradiating tissue which has been removed from a patient for the purpose of later being returned into the patient. The ex vivo configured light probe 42 has a handle 44, preferably a form fitting handle configured to allow the effective manual manipulation of the probe 42. The light probe 42 configured for external applications also has a shaft housing 46 surrounding a light guide 30 and a light guide terminator 34. An optical coupler 28 channels the light from the light delivery cable 24 and preferably allows the light probe 42 to be selectively detached from the light delivery cable 24 when desired.

Alternate embodiments employ as a light source, a lamp, such as a high intensity argon lamp. In these alternate embodiments, the UV radiation delivery system further includes a wavelength selecting device, such as a dichroic mirror and/or optical filter, set to transmit long wavelength UV and reject unwanted light wavelengths. In these embodiment, the wavelength selecting device and the dichroic mirror are preferably contained in the same housing as the light source.

Figure 6:
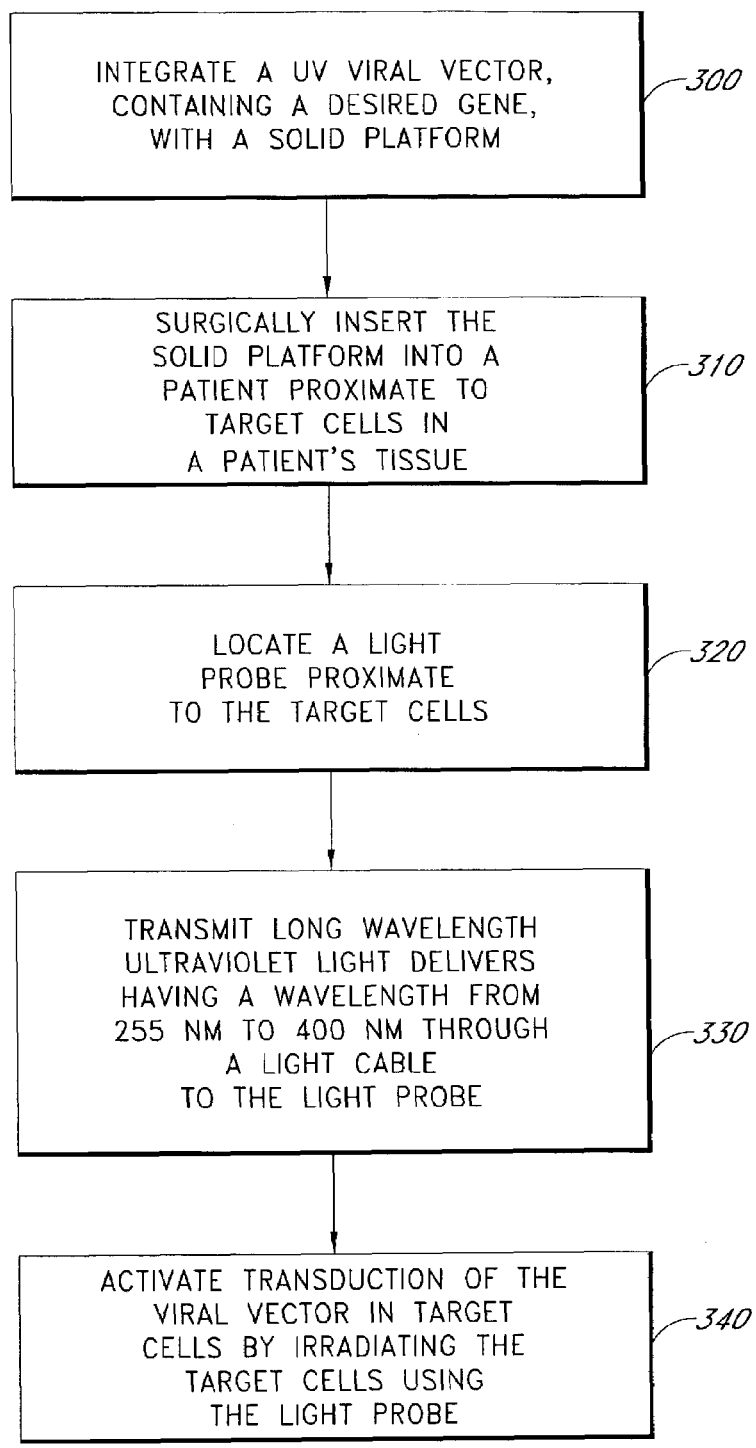
FIG. 6 is a flowchart of a method of treating a patient's tissue using a light activated viral vector and a solid platform.

As shown in FIG. 3, an injecting device 36 having a housing 38 and a plunger mechanism 40 is preferably employed in conjunction with the UV radiation delivery system of FIGS. 2 and 2B. Preferably, the injecting device 36 is configured for delivering a UV activated viral vector, such as r-AAV, to the target site using minimally invasive surgical techniques. In alternate preferred embodiments, the injecting device can be configured to inject an implant or solid platform to a target site in a patient (FIG. 6).

Surgery tools, other than injecting device shown in FIG. 3, which can be involved in certain preferred embodiments include a cannula, a trochar and other tools which the skilled artisan would recognize as being advantageous in conjunction with the embodiments provided herein.

Figure 4:
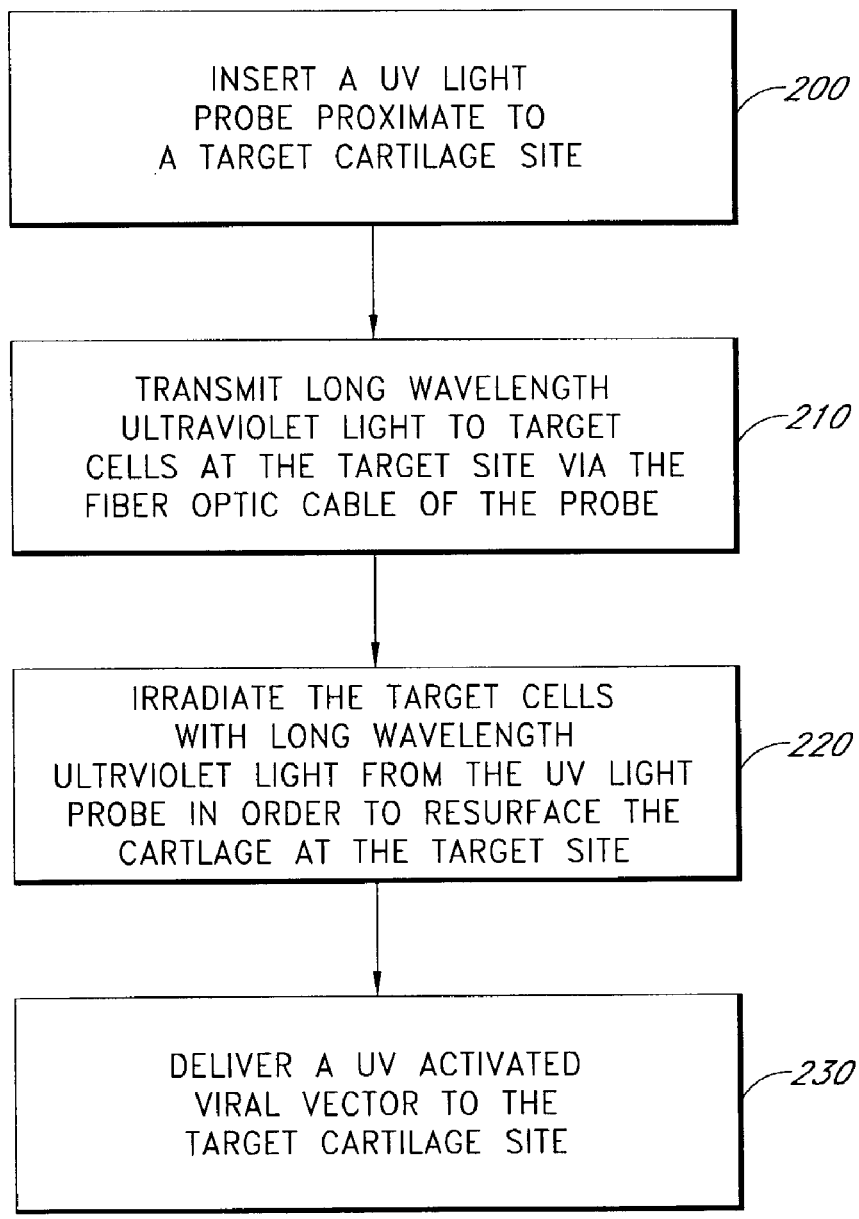
FIG. 4 is a method of treating a patient's cartilage using a UV activated viral vector and a long wavelength UV radiation system, in accordance with yet another embodiment of the present invention.

Referring to FIG. 4, a method is provided for the treatment of damaged cartilage tear. A UV probe is inserted 200 proximate to a cartilage target site. Preferably, if desirable, torn cartilage is removed via standard arthroscopy. Long wavelength ultraviolet light (i.e., greater than or equal to 255 nm) is transmitted 210 to the target cells via the fiber optic cable of the UV probe and the target cells are irradiated 220 with the long wavelength ultraviolet light in order to effectuate the resurfacing of the target cartilage site. A UV activated viral vector, such as r-AAV, is delivered 230 proximate to the target site, preferably by injection. It should be noted that the method of FIG. 4 may be performed in other preferred embodiments in a different order than the textually outlined above.

Referring to FIGS. 5A-5E, alternate preferred embodiments provide an implant system and methods for use thereof including the use of implants which serve as solid platforms at the target site (e.g., to create temporary mechanical rigidity between vertebra) while the target cells respond to the introduction of the desired gene into the patient's tissue. Preferably, these carefully engineered implants can be expandable in order to allow insertion through a minimal incision. In addition, these implants can be formed in a number of shapes, including (but not limited to) an unfolding geodosic dome 42 or tetrahedron (not shown), umbrella/dome (not shown), an expanding cylinder 44, and springs which uncoil to increase diameter. Expanding cylinder 44 is shown in a compacted shape in FIG. 5A and an expanded state in FIG. 5B (and also FIG. 5E), while unfolding geodosic dome 42 is shown in a compacted shape in FIG. 5C and an expanded state in FIG. 5D. Preferably, these implants are produced with implant integrated UV activated viral vector. For example, r-AAV can be integrated with the implant through bonding or coating the r-AAV to the implant, absorbing the r-AAV into the implant, and/or baking the r-AAV to the implant surface. In alternate preferred embodiments the implant is delivered to a target site separate from the UV activated viral vector.

FIG. 5E shows a solid platform 44, to which a UV activated viral vector is preferably integrated, placed between two vertebra 50 in order to facilitate the rebuilding or repair of the intervertebral disc 48. These solid platforms are preferably designed as surgical implants. Non-limiting examples of solid platforms with which UV activated viral vectors could be integrated include spinal spacers, as shown in FIG. 5E, and also total joint replacements such as hip implants, coronary stints and other surgical implants. These examples are provided only for illustrative purposes and should not be considered in any way to limit the present invention. Certain preferred embodiments of the present invention include a UV activated viral vector integrated with a solid platform designed to facilitate the infection of cells proximate to the target site at which the solid platform is inserted. In an alternative embodiment, the vector is delivered to the target site in a step separate from the insertion of the implant.

It should be understood that structural support implants incorporating such conventional structures as, for example, but not limited to, plates, rods, wire, cables, hooks, screws, are also advantageously useful with preferred embodiments provided herein. The support structure may be formed from material such as, but not limited to, metal, carbon-fiber, plastic, and/or reabsorbable material.

FIG. 6 provides a method of treating a patient using UV activated viral vector in conjunction with a solid platform. A UV activated viral vector containing a desired gene is integrated 300 with a solid platform. Preferably, the vector is integrated with the solid platform by bonded, baked, coated, and/or absorbing. The solid platform is then inserted 310 into a patient proximate to target cells in a patient's tissue. A light probe is located 320 proximate to the target cells and long wavelength ultraviolet light, having a wavelength from 225 nm to 400 nm, is transmitted through a light delivery cable, such as a fiber optic cable or bundle, to the light probe 330. The transduction of the viral vector is activated 340 by irradiating the target cells using the light probe.

It should be noted that the method of FIG. 6, and the other methods provided herein, may depending on the desired order and outcome, be performed in other preferred embodiments in a different order than the textually outlined herein.

Embodiments of the present invention include both in vivo and ex vivo applications. In the ex vivo application the long wavelength UV light dose is applied to cells or biological material external to the patient and then delivered, preferably through injection, to the desired site of treatment. In the in vivo application the LAGT probe and the UV activated viral vector are preferably introduced to the treatment site using minimally invasive surgical techniques, such as stab incisions. Alternate in vivo embodiments employ direct visualization surgical techniques.

A UV activated viral vector is any virus, or recombinant thereof, whose replication is regulated by ultraviolet light. Preferred embodiments of UV activated viral vectors are viruses with single stranded DNA, the virus being capable of allowing a therapeutically significant increase in virus transduction when a virus infected target cell is exposed to a therapeutic does of ultraviolet radiation. More preferred embodiments include UV activated viral vectors capable of infecting non-dividing cells, effectuating sustained target gene expression, eliciting a low immune response to the vector, and possessing an ability to transduce a large variety of tissues.

Proof of principle experiments, both ex vivo and in vivo based, are currently under way and can determine the optimal wavelengths for activating the gene therapy. The determination of more preferred wavelengths is based on among other factors, the ability to effectively penetrate a target cell, ease and efficiency of fiber optic transmission, the ability to trigger r-AAV transduction, and the length of time a patient must be exposed to receive a therapeutic dose of ultraviolet radiation. Preferably, the LAGT system delivers long wavelength ultraviolet radiation in the range of 315 nm to 400 nm. Current experiments support the use of ultraviolet radiation having a wavelength from 315 nm to 355 nm, more particularly about 325 nm, but it is believed that these experiments will ultimately support ultraviolet radiation having a wavelength from 315 nm to 400 nm. In addition, alternate embodiments employ a laser which produces ultraviolet radiation having a wavelength of about 290 nm. Once specific wavelengths are determined, the disclosed components can be optimized for these specific wavelengths.

The wavelength of the ultraviolet light generated in order to activate UV activated viral vector transduction, including r-AAV transduction, in target cells is preferably 255, 256, 258, 265, 275, 285, 290, 295, 305, 314, 325, 335, 345, 355, 365, 375, 385, 395, or 400 nanometers. More preferably, the wavelength of the ultraviolet light is 290, 295, 300, 305, 310, 315, 316, 317, 322, 325, 327, 332, 337, 342, 347, 352, 357, 362, 367, 372, 377, 382, 387, 392, 393, 394, 395, 396, 397, 398, or 399 nanometers. Most preferably, the wavelength of the ultraviolet light is 325 nanometers.

Tables 1-3 are charts of example growth factors, signaling molecules and/or transcription factors which desired genes, selected based on the desired use (e.g., implant integrated vs. in solution) and outcome (e.g., osteo-integration, spine fusion, perioprosthetic osteolysis, and/or cartilage repair/regeneration) inserted into a UV activated viral vector could encode for. The lists contained in Tables 1-3 are provided for illustrative purposes and should not be taken as limiting the embodiments of the invention in any way.

TABLE 1 osteo-integration and/or spine fusion:

(a) GROWTH FACTORS

Transforming Growth Factor beta (TGFb) 1, 2 and 3
bone morphogenetic protein (BMP) 1, 2, 4, 6 and 7
parathyroid hormone (PTH) parathyroid hormone related peptide (PTHrP)
fibroblast growth factor (FGF) 1, 2
insulin-like growth factor (IGF)

(b) SIGNALING MOLECULES AND TRANSCRIPTION FACTORS

LMP-1
Smad 1, 5, 8 dominant-negative Smad 2, 3
Smurf2
Sox-9
CBFA-1
ATF2

TABLE 2 perioprosthetic osteolysis:

soluble tumor necrosis factor receptors TNFR, TNFR:Fc
osteoprotegerin (OPG)
interleukin-1 receptor antagonist (IL-1RA), IL-1RII:Fc
interleukin-4, 10 and viral IL-10

TABLE 3

12/21 LAGT for cartilage:

(a) GROWTH FACTORS

Transforming Growth Factor beta (TGFb) 1, 2 and 3
bone morphogenetic protein (BMP) 1, 2, 4, 6 and 7
parathyroid hormone (PTH) parathyroid hormone related peptide (PTHrP)
fibroblast growth factor (FGF) 1, 2
insulin-like growth factor (IGF)
osteoprotegerin (OPG)

(b) SIGNALING MOLECULES AND TRANSCRIPTION FACTORS

Sox9
Smad 2, 3, dominant-negative Smad 1, 5, 8
Smurf 1, 2
ATF2
CREB

The results of a completed proof of principle experiment are shown below in Example 1.

EXAMPLE 1

I. Methods
  A. Isolation of Human Mesenchymal Stem Cells
  Human Mesenchymal Stem Cells (hMSC) were isolated from patient blood samples harvested from the iliac crest. The blood samples were diluted in an equal volume of sterile Phosphate Buffered Saline (PBS). The diluted sample was then gently layered over 10 ml of Lymphoprep (Media Prep) in a 50 ml conical tube (Corning). The samples were then centrifuged at 1800 rpm for 30 minutes. This isolation protocol is a standard laboratory technique, and the resulting gradient that formed enabled the isolation of the hMSCs from the layer immediately above the Lymphoprep. The isolated fraction was placed into a new 50 ml conical tube, along with an additional 20 ml of sterile PBS. The sample was centrifuged at 1400 rpm for 8 minutes. The supernatant was removed the cell pellet was resuspended in 20 ml for fresh PBS, and centrifuged again for 8 minutes at 1400 rpm. Afterwards the supernatant was removed, the cell pellet was resuspended in 10 ml of Dulbecco's Modified Eagle Medium (DMEM) with 10% Fetal Bovine Serum (FBS) and 1% Penicillin/Streptomycin (P/S) (Invitrogen). The hMSCs were grown and passed as necessary in a 37°/5% $CO_2$, water-jacketed incubator (Forma Scientific).

B. 325 nm UV treatment of Human Mesenchymal Stem Cells

Prior to irradiation, hMSCs were plated at a density of $5\times10^4$ cells/well in 12-well plates. The cells were allowed to sit down overnight. The next morning the media was removed immediately prior to irradiation. The cells were irradiated at various doses (500 $J/m^2$, 1000 $J/m^2$, 3000 $J/m^2$, 6000 $J/m^2$, or 10,000 $J/m^2$) of 325 nm UV light using a helium-cadmium laser system (Melles Griot). After irradiation, fresh media, either with or without recombinant adeno-associated virus was added to the wells.

C. Infection of Human Mesenchymal Stem Cells with Recombinant Adeno-Associated Virus Infections were carried out in 12-well dishes. The cells were infected at various multiplicities of infection (MOIs=10, 100, and 1000), using a recombinant adeno-associated virus carrying the bacterial β-galactosidase reporter gene (rAAV-LacZ via UNC-Chapel Hill Gene Therapy Vector Core Facility). After being irradiated, the cells were infected with the predetermined amount of virus in a total volume of 500 µl of DMEM/10% FBS/1% P/S. Two hours after the initial infection, and additional 1 ml of media was added to the cultures. The cultures were then allowed to incubate (37°/5% $CO_2$) for forty-eight hours before harvest for analysis.

D. Quantifying Recombinant Gene Expression

Forty-eight hours after infection, the cells were harvested; cell lysates were made and analyzed using a commercially available Luminescent β-gal Reporter System. (BD Biosciences), Briefly, experimental cell samples were removed from the 12-well dish using 0.25% Trypsin-EDTA. The cell suspension was transferred to a 1.5 ml conical tube and the cells were pelleted via a 15 second centrifugation at 13,000 rpm. The cell pellet was washed using two successive rounds of resuspension in ice cold PBS and pelleting for 15 seconds at 13,000 rpm. The final pellet was resuspended in 75 µl of Lysis Buffer (100 mM $K_2HPO_4$, 100 mM $KH_2PO_4$, 1 M DTT) and subjected to three rounds of freeze/thaw in an isopropanol dry ice bath and a 37° water bath. The lysates were centrifuged for a final time for 5 minutes at 13,000 rpm. Aliquots (15 µl) of the resulting supernatant were incubated with the provided substrate/buffer solution for one hour and then analyzed using a standard tube luminometer. The read out of this analysis is expressed in Relative Light Units (RLU) in the Results section.

II. Results

A. Exposure to 325 nm UV Increased the Level of Reporter Gene Expression

Figure 7:
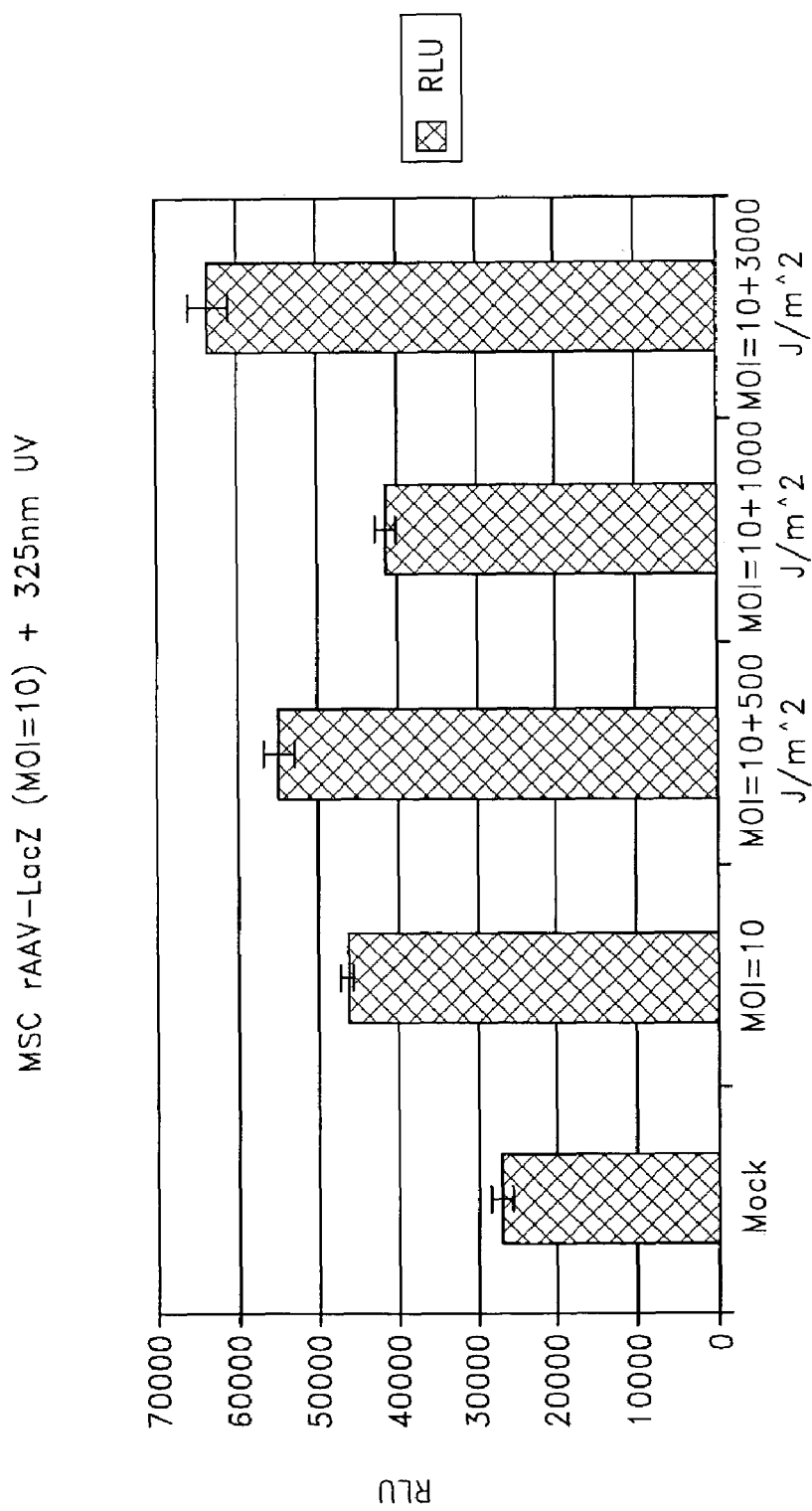
FIGS. 7-9 are graphs of the results of the proof of principle experiment of Example 1.
Figure 8:
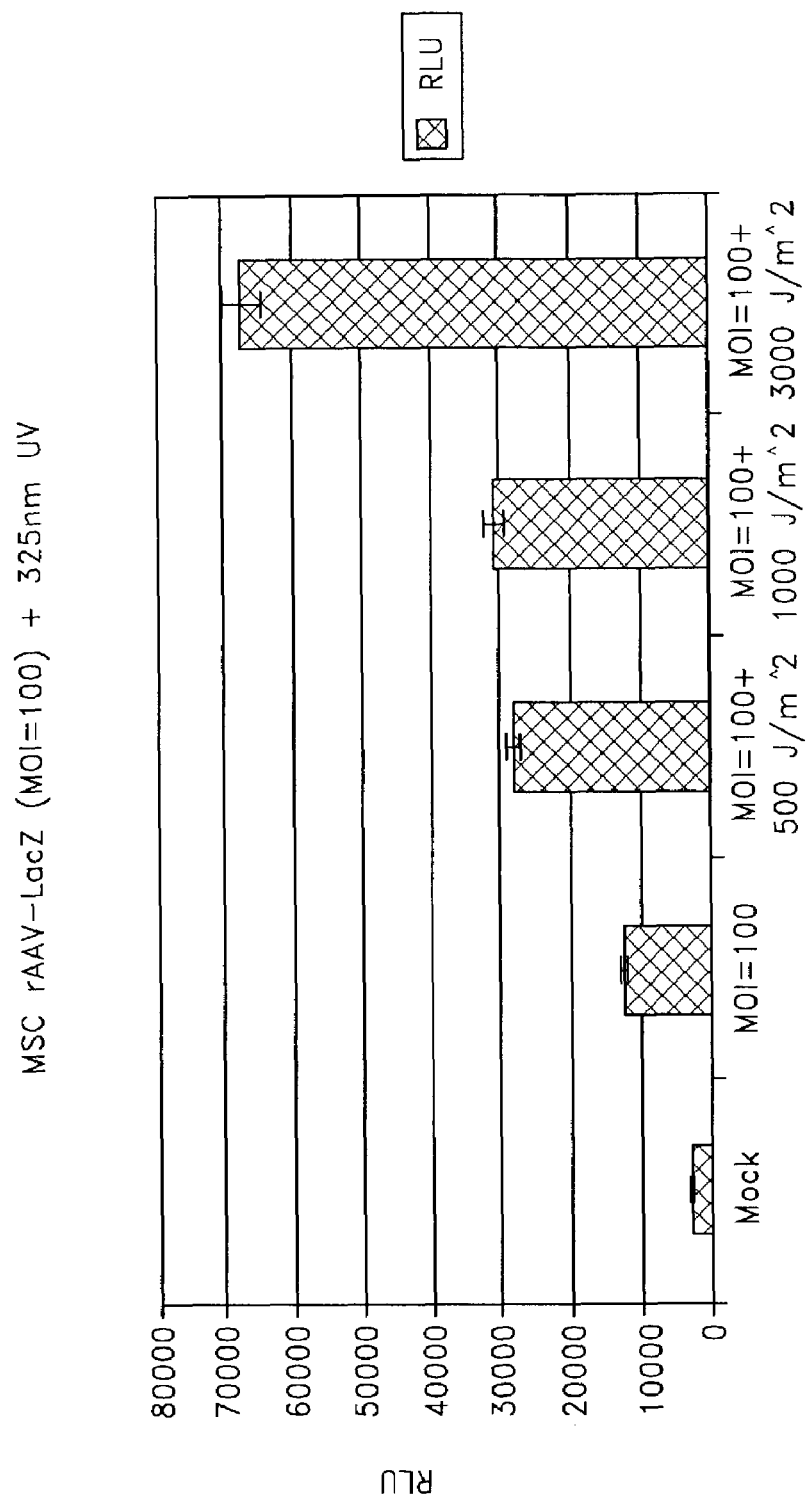
Figure 9:
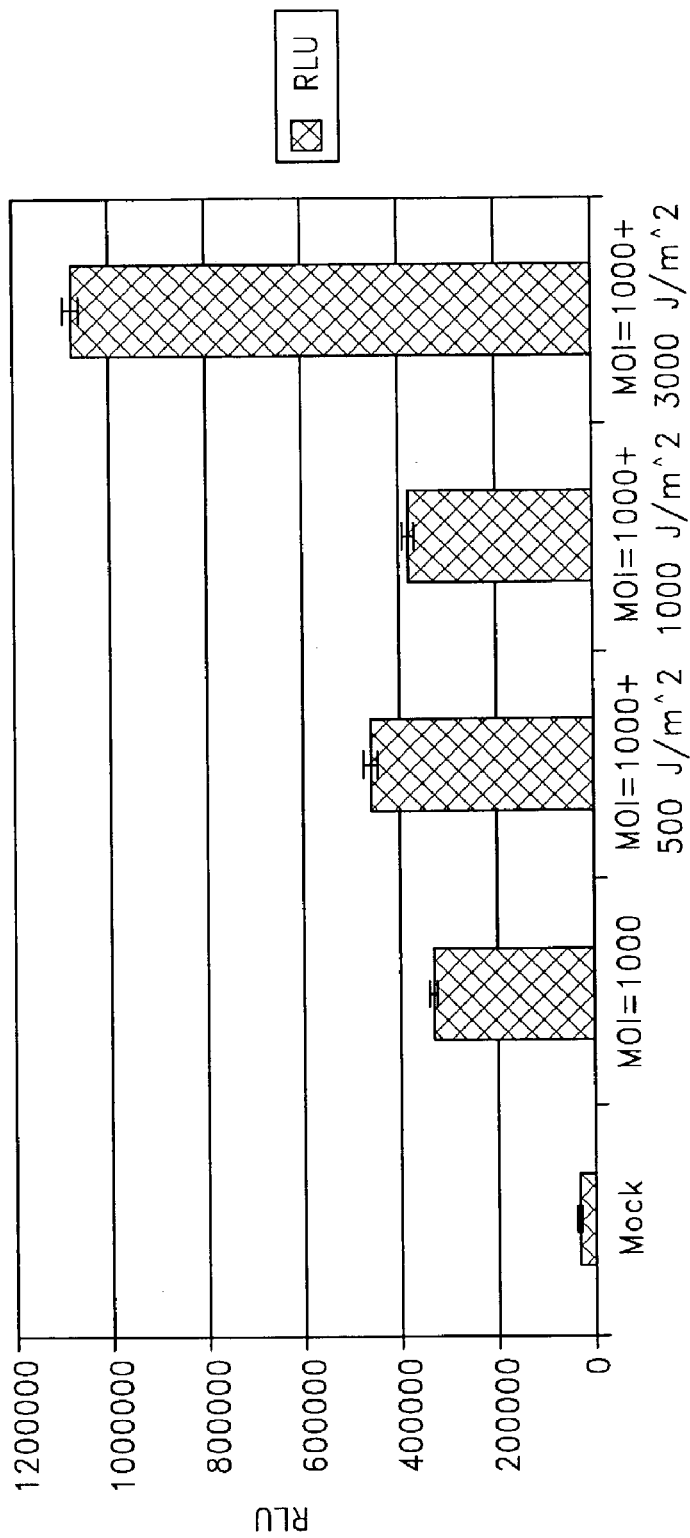

Exposure to 325 nm UV prior to infection with rAAV-LacZ had a dose dependent increase in LacZ reporter gene expression at each of the MOI's used. The controls for each experiment were as follows: Mock (cells alone, no treatment) and cells treated with each of the various UV dosages (500 $J/m^2$, 1000 $J/m^2$, 3000 $J/m^2$, 6000 $J/m^2$, which had RLU levels consistent with the Mock cultures (data not shown). Statistical significance was calculated using the Student T-Test. The results are shown in FIGS. 7-9.

Although this invention has been disclosed in the context of certain preferred embodiments and an Example, it will be understood by those skilled in the art that the present invention extends beyond the specifically disclosed embodiments to other alternative embodiments and/or uses of the invention and obvious modifications thereof. It will be appreciated, however, that no matter how detailed the foregoing may appear in text, the invention may be practiced in many ways. Thus, it is intended that the scope of the present invention herein disclosed should not be limited by the particular disclosed embodiments described above, but should be determined only by a fair reading of the claims that follow and any equivalents thereof.

We claim:

1. A method of introducing an ultraviolet light activated viral vector into a patient's tissue comprising:
    locating a light probe proximate to a target cell, wherein the target cell is selected from the group consisting of a chondrocyte cell and a mesenchymal cell;
    transmitting UVA wavelength ultraviolet light through a light delivery cable to the light probe, wherein an intensity of the UVA light transmitted is equal to or greater than 500 $J/m^2$ and equal to or less than 10,000 $J/m^2$;
    activating transduction of an ultraviolet light activated viral vector in the target cell using the light probe, wherein the ultraviolet light activated viral vector comprises an adeno-associated viral vector; and
    delivering the ultraviolet light activated viral vector proximate to the target cell.

2. The method according to claim 1, wherein the UVA wavelength ultraviolet light transmitted to the light probe has a wavelength of about 325 nm.

3. The method according to claim 1, wherein transmitting the light occurs before delivering the vector.

4. The method according to claim 1, wherein transmitting the light occurs after delivering the vector.

5. The method according to claim 1, wherein the transduction of the viral vector is activated by locally administering to the target cell UVA wavelength ultraviolet light generated by a laser.

6. The method according to claim 1, wherein the intensity of the UVA light used is more than 1000 $J/m^2$ and less than 6000 $J/m^2$.

7. The method according to claim 1, further comprising:
    spacing a target site, where the target cell is located, with an implant; and
    injecting the ultraviolet light activated viral vector.

8. The method of claim 7, wherein spacing comprises attaching a structural support implant to bone.

9. The method according to claim 1, further comprising:
    bonding a ultraviolet activated viral vector to a solid platform configured to be surgically inserted in a patient for therapeutic purposes; and
    surgically inserting the solid platform into a patient.

10. The method according to claim 9, wherein the ultraviolet light activated viral vector is recombinant adeno-associated virus (r-AAV).

11. The method according to claim 10, further comprising the step of discretely inserting a light probe proximate to the solid platform through a minimally invasive surgical technique into a patient.

12. The method according to claim 1, wherein the viral vector is recombinant adeno-associated virus (r-AAV).

13. The method according to claim 1, wherein delivering the ultraviolet light activated viral vector proximate to the target cell comprises infecting the target cell with the ultraviolet light activated viral vector.

14. The method according to claim 12, further comprising:
removing the tissue from the patient's body before exposing the tissue to the recombinant adeno-associated virus; and
returning the tissue to the patient's body.

15. The method according to claim 12, further comprising:
exposing the tissue to the recombinant adeno-associated virus without first removing the tissue from the patient's body.

16. The method according to claim 12, wherein the UVA wavelength ultraviolet light transmitted to the light probe has a wavelength from about 320 nm to about 400 nm.

17. The method according to claim 12, wherein the UVA wavelength ultraviolet light transmitted to the light probe has a wavelength from about 380 nm to about 330 nm.

18. The method according to claim 12, wherein the UVA wavelength ultraviolet light transmitted to the light probe has a wavelength of no more than 355 nm.

19. The method according to claim 12, wherein the UVA wavelength ultraviolet light transmitted to the light probe has a wavelength of about 325 nm.

20. The method according to claim 12, wherein the UVA wavelength ultraviolet light transmitted to the light probe has a wavelength of about 322, 325, 327, 332, 337, 342, 347, 352, 357, 362, 367, 372, 377, 382, 387, 392, 393, 394, 395, 396, 397, 398, or 399 nm.

21. The method according to claim 12, wherein the UVA wavelength ultraviolet light transmitted to the light probe is selected from the group consisting of 325, 335, 345, 355, 365, 375, 385, 395, and 400 nm.

22. The method according to claim 12, wherein the light probe is designed for arthroscopic surgery.

23. The method according to claim 22, further comprising the step of discretely inserting the light probe through minimally invasive surgical techniques into a patient.

24. The method according to claim 23, wherein the target cell is the chondrocyte cell.

* * * * *

UNITED STATES PATENT AND TRADEMARK OFFICE
CERTIFICATE OF CORRECTION

PATENT NO.        : 7,524,327 B2                                                Page 1 of 1
APPLICATION NO.   : 10/357271
DATED             : April 28, 2009
INVENTOR(S)       : Schwarz et al.

It is certified that error appears in the above-identified patent and that said Letters Patent is hereby corrected as shown below:

On the Title Page

Item [*] Notice:     Subject to any disclaimer, the term of this patent is extended or adjusted under 35 USC 154(b) by 222 days Delete the phrase "by 222 days" and insert -- by 443 days --

Signed and Sealed this

Eleventh Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,524,327 B2
APPLICATION NO. : 10/357271
DATED : April 28, 2009
INVENTOR(S) : Edward M. Schwarz et al.

It is certified that error appears in the above-identified patent and that said Letters Patent is hereby corrected as shown below:

At column 1, under the "Government Interest" section, change "NIH Contract #AR45971, an ROI grant awarded by NIAMS"," to -- grant numbers AR045971 and HL059921 awarded by the National Institutes of Health --.

Signed and Sealed this
Ninth Day of April, 2013

Teresa Stanek Rea
*Acting Director of the United States Patent and Trademark Office*